United States Patent [19]

Hackney et al.

[11] Patent Number: 4,672,072

[45] Date of Patent: Jun. 9, 1987

[54] POUR-ON FORMULATIONS

[75] Inventors: Ronald J. Hackney, Croydon Park; James J. Guinan, Concord, both of Australia

[73] Assignee: Wellcome Australia Limited, New South Wales, Australia

[21] Appl. No.: 710,946

[22] Filed: Mar. 13, 1985

Related U.S. Application Data

[63] Continuation of Ser. No. 475,513, Mar. 15, 1983, abandoned.

[30] Foreign Application Priority Data

Mar. 16, 1982 [AU] Australia ................. PF3147

[51] Int. Cl.$^4$ ................. A61K 31/425; A61K 31/215
[52] U.S. Cl. ................................. 514/368; 514/531
[58] Field of Search ................. 514/368, 531

[56] References Cited

U.S. PATENT DOCUMENTS

| | | | |
|---|---|---|---|
| 3,641,245 | 2/1972 | Epstein et al. | 424/188 |
| 4,070,476 | 1/1978 | Brooker et al. | 424/304 |
| 4,096,262 | 6/1978 | Andrews et al. | 424/270 |
| 4,183,948 | 1/1980 | Huff | 424/304 |
| 4,206,227 | 6/1980 | Mues et al. | 424/304 |
| 4,341,760 | 7/1982 | Matthewson | 424/45 |

FOREIGN PATENT DOCUMENTS

| | | |
|---|---|---|
| 0489412 | 12/1977 | Australia . |
| 0490027 | 1/1978 | Australia . |
| 0499160 | 4/1979 | Australia . |
| 0506372 | 12/1979 | Australia . |
| 0017810 | 4/1979 | European Pat. Off. . |
| 1176799 | 1/1970 | United Kingdom . |
| 2065475A | 12/1980 | United Kingdom . |
| 1591105 | 6/1981 | United Kingdom . |
| 1591106 | 6/1981 | United Kingdom . |
| 2079603A | 7/1981 | United Kingdom . |
| 2085302A | 10/1981 | United Kingdom . |
| 2088212A | 11/1981 | United Kingdom . |

OTHER PUBLICATIONS

Van Der Veken, et al., Australian Patent Abstract, 71322/81.
Evans et al—Chem. Abst., vol. 99 (1983), p. 43566a.

Primary Examiner—Sam Rosen
Attorney, Agent, or Firm—Donald Brown

[57] ABSTRACT

A pour-on formulation which allows the simultaneous control of internal and external parasites in mammals by a single localized superficial application comprises a pyrethroid in admixture with a thiazole or salt or ester thereof.

17 Claims, No Drawings

POUR-ON FORMULATIONS

This application is a continuation of application Ser. No. 475,513 filed Mar. 15, 1983, now abandoned.

The present invention relates to the simultaneous control of internal and external parasites in mammals by means of a single localised superficial application of a pyrethroid together with a thiazole.

It is known to control external parasites on mammals such as sheep by the localised application of a pour-on formulation containing a pyrethroid. A pour-on formulation is generally a liquid formulation which, when applied locally as a line or spot to the external surface of the mammal, acts to protect the whole outer surface of the mammal against external parasites. Such a formulation is disclosed in our Australian Patent Application No. 77004/81.

It is also known to use a thiazole, such as levamisole (also called tetramisole), for controlling internal parasites. The thiazole acts systematically.

In the control of parasites, it is generally necessary to take measures to combat both internal and external parasites. In the past this has necessitated two separate operations, for example drenching to control internal parasites and dipping or use of a pour-on formulation to control external parasites.

It is an object of the present invention to control both internal and external parasites by a single localised superficial application.

The present invention provides a formulation for control of both internal and external parasites on a mammal by localised application, which comprises a pyrethroid, a thiazole or salt or ester thereof, and a topically-acceptable carrier.

The invention further provides a method of simultaneously controlling internal and external parasites which comprises making a localised external application of a pyrethoid and a thiazole onto a mammal. Generally, a liquid formulation is applied. However, the active agents may also be applied in the form of a powder, paste or gel.

The present invention is particularly concerned with the treatment of animals of agricultural significance such as sheep, goats, cattle, horses and pigs, but is not limited thereto. The formulation is particularly effective on merino sheep. Usually the formulation will be applied to a sheep shortly after shearing, generally within 24 hours.

The pyrethroids have the formula

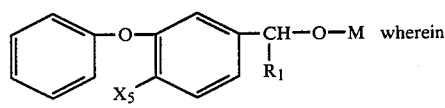 wherein

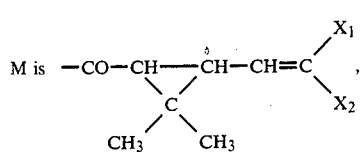

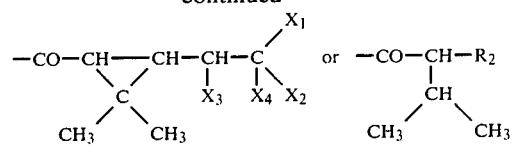

and wherein $X_1$ to $X_4$ are independently selected from halo, $C_1-C_4$ alkyl, halogen-substituted $C_1-C_4$ alkyl, and halogen-substituted phenyl;

$X_5$ is —H or halo;

$R_1$ is —H or cyano; and $R_2$ is halogen-substituted phenyl.

Particularly preferred compounds are presented in Tables I to III.

TABLE I

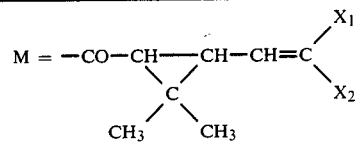

| No. | $X_1$ | $X_2$ | $X_3$ | $X_4$ | $X_5$ | $R_1$ | trivial name |
|---|---|---|---|---|---|---|---|
| 1 | Cl | Cl | — | — | H | H | permethrin |
| 2 | $CH_3$ | $CH_3$ | — | — | H | H | phenothrin |
| 3 | Br | Br | — | — | H | CN | deltamethrin |
| 4 | Cl | Cl | — | — | H | CN | cypermethrin |
| 5 | Cl | $CF_3$ | — | — | H | CN | cyhalothrin |
| 6 | Cl | —C₆H₄—Cl | — | — | F | CN | flumethrin |
| 7 | Cl | Cl | — | — | F | CN | cyfluthrin |
| 8 | $CH_3$ | $CH_3$ | — | — | H | CN | cyphenothrin |

TABLE II

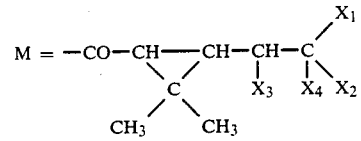

| No. | $X_1$ | $X_2$ | $X_3$ | $X_4$ | $X_5$ | $R_1$ | trivial name |
|---|---|---|---|---|---|---|---|
| 9 | Br | Br | Br | Br | H | CN | tralomethrin |
| 10 | Cl | Cl | Br | Br | H | CN | tralocythrin |

TABLE III

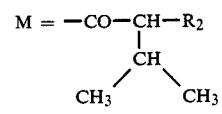

| No. | $R_2$ | $X_5$ | $R_1$ | trivial name |
|---|---|---|---|---|
| 11 | —C₆H₄—Cl | H | CN | fenvalerate |

The thiazoles have the formula

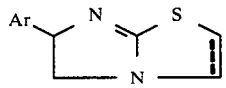

wherein Ar is selected from phenyl, benzyl, and naphthyl, optionally substituted with a $C_1$–$C_5$ alkyl, halo or nitro group, provided that the dotted line indicates a bond which is optionally present.

The compound wherein Ar is phenyl is named levamisole (the L.-isomer) or tetramisole (mixture of D- and L-isomers). The thiazole may be present as the free base, as the acid addition salt e.g. the hydrochloride, or as the salt of a fatty acid, e.g. the oleate.

Generally, the pour-on formulation is applied by pouring-on along the back of the animal. Alternatively, it may be applied by means of a localised spray. Thus, the formulation may be in the form of an aerosol, including a propellant such as liquid carbon dioxide, a fluorocarbon, a liquified or compressed gas.

It is a particular advantage of the use of pour-on formulations that only small volumes of the formulation need to be applied. Depending on the size of the animal, the volume applied will generally lie in the range 2–15 ml.

Depending on the efficacy of the particular active agent used, the formulation will generally contain from 0.1 to 500, preferably 1 to 250 mg/ml of each of the active pyrethroid and thiazole agents. The weight ratio of pyrethroid: thiazole will usually lie in the region 1:5 to 1:40. Usually from 1 to 500 mg/kg body weight of each active agent will be applied.

The pyrethroid is effective against external parasites and insects, including lice, ticks, keds, mites and flies. In particular, it is effective against cattle lice (e.g. *Damalinia bovis* and *Linognathus vituli*) and flies and against sheep lice (*Damalinia ovis*), keds and flies. The thiazole is dermally absorbed into the blood stream and acts systemically against internal parasites. Thus, surprisingly a pour-on formulation is provided having a combination of both superficial and systemic activity.

Deltamethrin is the preferred pyrethroid, and levamisole is the preferred thiazole.

The pour-on formulation may comprise an aqueous or non-aqueous liquid carrier, and the active agents (i.e. the pyrethroid and the thiazole) may be present in the form of a suspension, dispersion, emulsion, or in the dissolved state. To avoid chemical interaction between the thiazole and the pyrethroid during storage, it is preferred that the active agents be present in separate phases within the carrier. This may be achieved by dissolving one active agent in the carrier, whilst the other is suspended, dispersed or emulsified. Alternatively, one or both of the active agents may be microencapsulated separately in wax beadlets according to known techniques.

The non-aqueous carrier may comprise one or more organic solvents, such as xylene, toluene, cyclohexanone, and a glycol. The carrier will be formulated to provide the desired degree of dermal penetration and superficial activity.

One preferred solvent system comprises 30–70 wt % xylene, 20–40 wt % cyclohexanone and 5–25 wt % vegetable oil.

Suitable glycols include ethylene glycol and propylene glycol, polyethylene glycols, polypropylene glycols, ethylene glycol - propylene glycol copolymers, alkyl ethers thereof and alkyl ether esters thereof of the general formula:

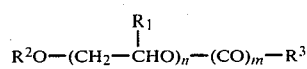

where
$R^1$ = $C_1$ alkyl or hydrogen,
$R^2$ = $C_1$–$C_5$ alkyl, hydrogen or —CO—$R^3$,
$R^3$ = $C_1$–$C_{12}$ alkyl,
n = 1–40, and
m = 0 or 1.

Diethylene glycol mono-n-butyl ether has been found to be particularly useful. Particularly, it has been found to have minimal adverse effect on the skin in terms of mild epidermal shedding seen with other solvents in some sheep.

The formulation may comprise suitable surfactants for stabilisation and to prevent undue run-off from the back of the animal.

Paraffin oils, vegetable oils, e.g. corn oil, peanut oil, castor oil, olive oil, can be added as viscosity modifiers and co-solvents.

Alkylamides and esters of fatty acids are useful formulation adjuncts e.g. n-butyl oleate, N,N-dimethyl oleamide and isopropyl myristate (IPM).

It has been found that the inclusion of an antioxidant such as 2,6-ditert-butyl-4-cresol (BHT) or 2-tert-butyl-4-methoxyphenol (BHA) has a useful stabilising effect on the active ingredients in formulations based on glycols, glycol ethers, glycol ether esters and cyclohexanone.

The formulation will usually also comprise a dyestuff to enable the treated mammals to be distinguished from the untreated. The dyestuff may be dissolved, suspended or dispersed in the carrier. Generally, the dyestuff is biodegradable so as to fade and not permanently mark the skin or fleece.

FORMULATIONS

Preferred formulations will now be described by way of example only as follows:

EXAMPLE 1

10.1 g deltamethrin (989 g/kg active) and 100 g levamisole were dissolved in the following:

| | |
|---|---|
| xylene | 55% by weight |
| cyclohexanone | 30% by weight |
| corn oil | 15% by weight |
| Sudan Red (oil soluble dye) | 50 ppm |

EXAMPLE 2

10.1 g deltamethrin (989 g/kg active) and 100 g levamisole were dissolved in diethylene glycol mono butyl ether and volume made to 1 liter.

EXAMPLE 3

10.1 g deltamethrin (989 g/kg) and 100 g levamisole were dissolved in the following:

| | |
|---|---|
| diethylene glycol mono butyl ether | 80% by weight |
| cyclohexanone | 20% by weight |

EXAMPLE 4

A pour-on formulation was made up which comprised 10 g deltamethrin and 200 g levamisole in one liter of xylene.

EXAMPLE 5

A pour-on formulation was made up which comprised 50.5 g cypermethrin (989 g/kg active) and levamisole oleate (equivalent to 200 g levamisole base) dissolved in diethylene glycol mono-butyl ether and the volume made up to 1 liter.

EFFICACY DATA

Trials were conducted to assess the efficiency of pour-on formulations in the control of internal and external parasites. The efficacy of levamisole was measured as a function of its mean blood plasma levels rsulting from dermal penetration. There is an established correlation between levamisole plasma levels and effectiveness against internal parasites. The efficacy of deltamethrin was assessed as a function of reduction in cattle lice (Damalinia bovis) populations.

A pour-on formulation comprising 200 g/l levamisole and 10 g/l deltamethrin in xylene was applied to cattle at a dosage of 20 mg levamisole and 1 mg deltamethrin per kilogram body weight as a stripe down the animal's back.

Levamisole: Control of Internal Parasites

A peak levamisole blood serum level of 1.75 micrograms/ml was recorded. At this level good control of internal parasites is known to be achieved.

Deltamethrin: Control of External Parasites

Cattle lice populations were monitored in a control group and a group treated with the formulation. The lice counts were scored as follows:

One side only of the animal is examined, at ten sites (head, neck, brisket, ears, top-line, mid-line, under-line, rump, escutcheon and tail) and the infestation at each site allotted points on the following scale:
1 Very light
2 Light
3 Light to moderate
4 Moderate
5 Moderate to heavy
6 Heavy The total point score is then added, the maximum possible being 60 points.

The results are given in Table 1.

Although there is a fall in lice population in the control group over the test period (probably due to heavy rain) some lice persisted; whereas in the treated group all lice were eliminated.

TABLE 1

| Group | Cattle Louse Counts (Damalinia bovis) | | |
|---|---|---|---|
| | Cattle Number | Pre-treatment | 6 Weeks |
| 1 Treated | 6 | 19 | — |
| | 10 | 19 | — |
| | 77 | 33 | — |
| | 82 | 14 | — |
| | 91 | 27 | — |
| 2 Untreated Control | 8 | 2 | — |
| | 11 | 23 | 10 |
| | 14 | 6 | — |
| | 79 | 16 | — |
| | 80 | 6 | 2 |
| | 83 | 29 | 5 |
| | 86 | 15 | — |
| | 88 | 17 | 1 |
| | 90 | 8 | 1 |

The claims defining the invention are as follows; we claim:

1. A pour-on formulation for simultaneous control of both internal and external parasites on a mammal by localized pour-on application of a small volume thereof to a localized surface area of the mammal; said formulation comprising;

(A) a pyrethroid of the formula

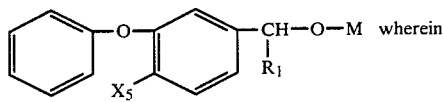

M is

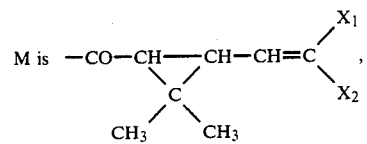

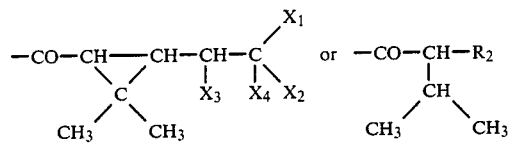

and wherein
$X_1$ to $X_4$ are independently selected from halo, $C_1$-$C_4$ alkyl, halogen-substituted $C_1$-$C_4$ alkyl, and halogen-substituted phenyl;
$X_5$ is —H or halo;
$R_1$ is —H or cyano; and
$R_2$ is halogen-substituted phenyl (B) a thiazole selected from the group consisting of levamisole, tetramisole and acid addition salts and fatty acid salts thereof, said pyrethroid and said thiazole each being present in an amount of 0.1 to 500 mg per ml of said formulation, and a topically acceptable pour-on carrier effective to minimize run-off of the applied formulation from said localized surface area of the mammal.

2. A formulation according to claim 1 wherein the pyrethroid is deltamethrin.

3. A formulation according to claim 1 wherein the pyrethroid is cypermethrin.

4. A formulation according to claim 1 wherein the pyrethroid is cyhalothrin.

5. A formulation according to claim 1 wherein the carrier is a mixture of xylene, cyclohexanone and corn oil.

6. A formulation according to claim 1 wherein the carrier is xylene.

7. A formulation according to claim 1 wherein the carrier is selected from ethylene glycol, propylene glycol, polyethylene glycols, polypropylene glycols or ethylene glycol-propylene glycol copolymers.

8. A formulation according to claim 1 wherein the carrier is an alkyl ether or alkyl ether ester of general formula:

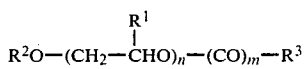

where
R$^1$ = methyl or hydrogen
R$^2$ = C$_1$-C$_5$ alkyl, hydrogen or —CO—R$^3$,
R$^3$ = C$_1$-C$_{12}$ alkyl
n = 1–40, and
m = 0 or 1.

9. A formulation according to claim 8 wherein the carrier is diethylene glycol mono-n-butyl ether.

10. A formulation according to claim 7 which further comprises an antioxidant selected from 2,6-ditertbutyl-4-cresol and 2-tert-butyl-4-methoxy phenol.

11. A formulation according to claim 1 wherein one of the pyrethroid and the thiazole or salt thereof is suspended, dispersed or emulsified in the carrier, whilst the other is dissolved.

12. A formulation according to claim 1 wherein the pyrethroid and the thiazole or salt thereof are separately suspended, dispersed or emulsified in the carrier.

13. A formulation according to claim 1 wherein one of the pyrethroid and the thiazole or salt thereof are separately encapsulated in wax beadlets.

14. A method of simultaneously controlling internal and external parasites on a mammal by the single localized application of a small volume of a pour-on formulation to a localized surface area of the mammal; said formulation comprising
(A) a pyrethroid of the formula

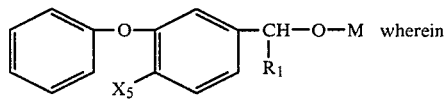

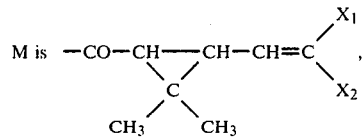

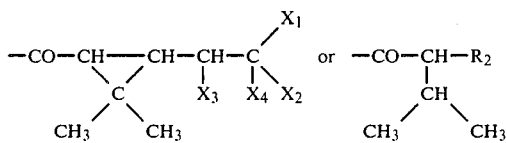

and wherein
X$_1$ to X$_4$ are independently selected from halo, C$_1$-C$_4$ alkyl, halogen-substituted C$_1$-C$_4$ alkyl, and halogen-substituted phenyl;
X$_5$ is —H or halo;
R$_1$ is —H or cyano; and
R$_2$ is halogen-substituted phenyl
(B) a thiazole selected from the group consisting of levamisole, tetramisole and acid addition salts and fatty acid salts thereof,
said pyrethroid and said thiazole each being present in an amount of 0.1 to 500 mg per ml of said formulation, and a topically acceptable pour-on carrier effective to minimize run-off of the applied formulation from said localized surface area of the mammal.

15. A pour-on formulation suitable for localized application to a small area of an amimal comprising permethrin and levamisole, said permethrin amd said levamisole, each being present in an amount of 0.1 to 500 mg/ml of said formulation.

16. A method of simultaneously controlling internal and external parisites on an animal which comprises applying to said animal an effective amount of a pour-on formulation comprising permethrin and levamisole, each being present in an amount of 0.1 to 500 mg/ml said formulation.

17. The method treating of preventing lice infestions of cattle, sheep, goats, horses and pigs which comprises topically applying to said cattle, sheep, goats, horses and pigs an effective amount of a pour-on formulation comprising permethrin and levamisole, each being present in an amount of 0.1 to 500 mg/ml of said formulation.

* * * * *